(12) United States Patent
Kang et al.

(10) Patent No.: US 10,695,039 B2
(45) Date of Patent: Jun. 30, 2020

(54) BIOTISSUE SAMPLING APPARATUS

(71) Applicant: National Cancer Center, Gyeonggi-do (KR)

(72) Inventors: Hyun Guy Kang, Seoul (KR); Kwang Gi Kim, Seoul (KR); Na Ri Yang, Gyeonggi-do (KR); Sang Bong Lee, Gyeonggi-do (KR)

(73) Assignee: NATIONAL CANCER CENTER, Goyang-si (KR)

( * ) Notice: Subject to any disclaimer, the term of this patent is extended or adjusted under 35 U.S.C. 154(b) by 22 days.

(21) Appl. No.: 14/648,685

(22) PCT Filed: Nov. 29, 2013

(86) PCT No.: PCT/KR2013/010963
§ 371 (c)(1),
(2) Date: May 29, 2015

(87) PCT Pub. No.: WO2014/084650
PCT Pub. Date: Jun. 5, 2014

(65) Prior Publication Data
US 2015/0305721 A1   Oct. 29, 2015

(30) Foreign Application Priority Data

Nov. 30, 2012  (KR) .......................... 10-2012-0138295
Jul. 8, 2013  (KR) .......................... 10-2013-0079977

(51) Int. Cl.
*A61B 10/02*  (2006.01)

(52) U.S. Cl.
CPC ...... *A61B 10/0275* (2013.01); *A61B 10/0283* (2013.01); *A61B 2010/0225* (2013.01)

(58) Field of Classification Search
CPC ............ A61B 10/0275; A61B 10/0283; A61B 2010/02; A61B 2010/0233; A61B 2010/0266; A61B 2010/0225
See application file for complete search history.

(56) References Cited

U.S. PATENT DOCUMENTS

| 5,830,152 | A | * | 11/1998 | Tao ..................... A61B 10/0233 600/562 |
| 6,022,324 | A | * | 2/2000 | Skinner ................ A61B 10/025 600/564 |

(Continued)

FOREIGN PATENT DOCUMENTS

EP  0243341 A2 * 10/1987 ......... A61B 10/0283

OTHER PUBLICATIONS

EP0243341 A2 Machine Translation.*

*Primary Examiner* — Sean P Dougherty
*Assistant Examiner* — Benjamin S Melhus
(74) *Attorney, Agent, or Firm* — Womble Bond Dickinson (US) LLP

(57) ABSTRACT

The following description provides a biotissue sampling apparatus comprising a housing, a firing button configured on a rear-end of the housing; a tube with an aspirating hole configured to inject medicine in a tissue according to a longitudinal direction of a lower end and extended from a front-end of a housing; and a needle assembly that may move from the tube to a biopsy region by a button thereby cut a solid tissue and store or aspire a fluid tissue.

20 Claims, 17 Drawing Sheets

(56) References Cited

U.S. PATENT DOCUMENTS

| | | | | |
|---|---|---|---|---|
| 6,162,203 | A * | 12/2000 | Haaga | A61B 10/0275 128/898 |
| 6,432,064 | B1 * | 8/2002 | Hibner | A61B 10/0275 128/897 |
| 6,702,760 | B2 * | 3/2004 | Krause | A61B 10/0233 600/564 |
| 7,156,815 | B2 * | 1/2007 | Leigh | A61B 10/0266 600/564 |
| 7,766,843 | B2 * | 8/2010 | Voegele | A61B 10/0275 600/567 |
| 8,992,481 | B2 * | 3/2015 | Mudd | A61M 5/14546 604/154 |
| 9,149,293 | B2 * | 10/2015 | Hardert | A61B 10/0266 |
| 9,282,948 | B2 * | 3/2016 | Melchiorri | A61B 10/0266 |
| 10,448,930 | B2 * | 10/2019 | McGhie | A61B 10/0233 |
| 2002/0183715 | A1 * | 12/2002 | Mantell | A61B 17/3496 604/506 |
| 2006/0089564 | A1 * | 4/2006 | Goldenberg | A61B 10/0233 600/566 |
| 2007/0197954 | A1 * | 8/2007 | Keenan | A61B 8/0833 604/20 |
| 2007/0297271 | A1 * | 12/2007 | Foster | A61B 17/8802 366/42 |
| 2009/0216151 | A1 * | 8/2009 | Speeg | A61B 10/0275 600/567 |
| 2012/0184873 | A1 * | 7/2012 | Jorgensen | A61B 10/0275 600/567 |
| 2013/0023790 | A1 * | 1/2013 | Schaeffer | A61B 10/0275 600/567 |

* cited by examiner

[Fig. 1 - PRIOR ART]
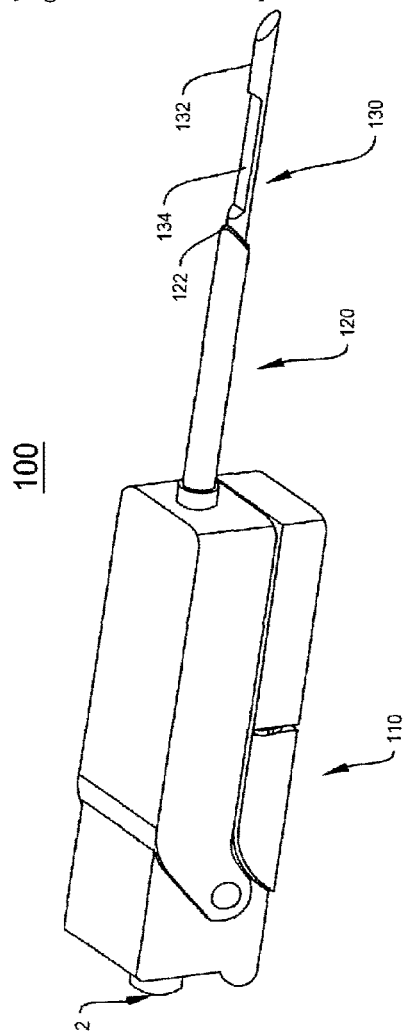
[Fig. 2a - PRIOR ART]
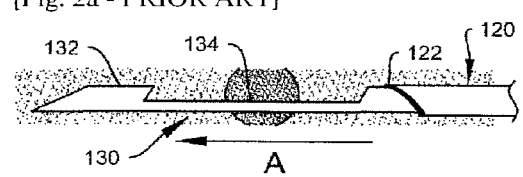
[Fig. 2b] - PRIOR ART
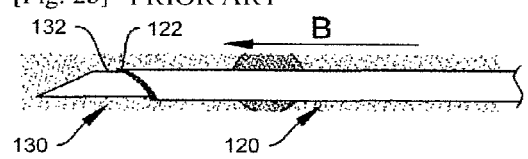

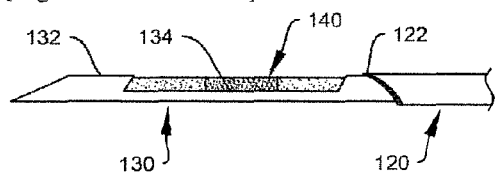
[Fig. 2c - PRIOR ART]
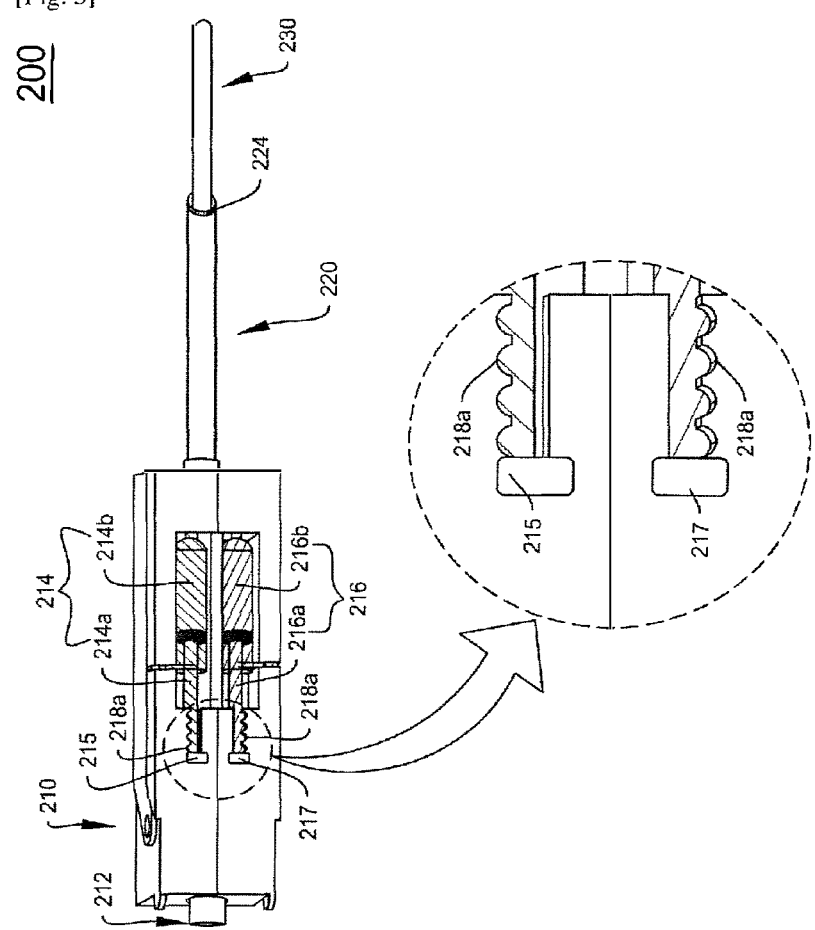
[Fig. 3]

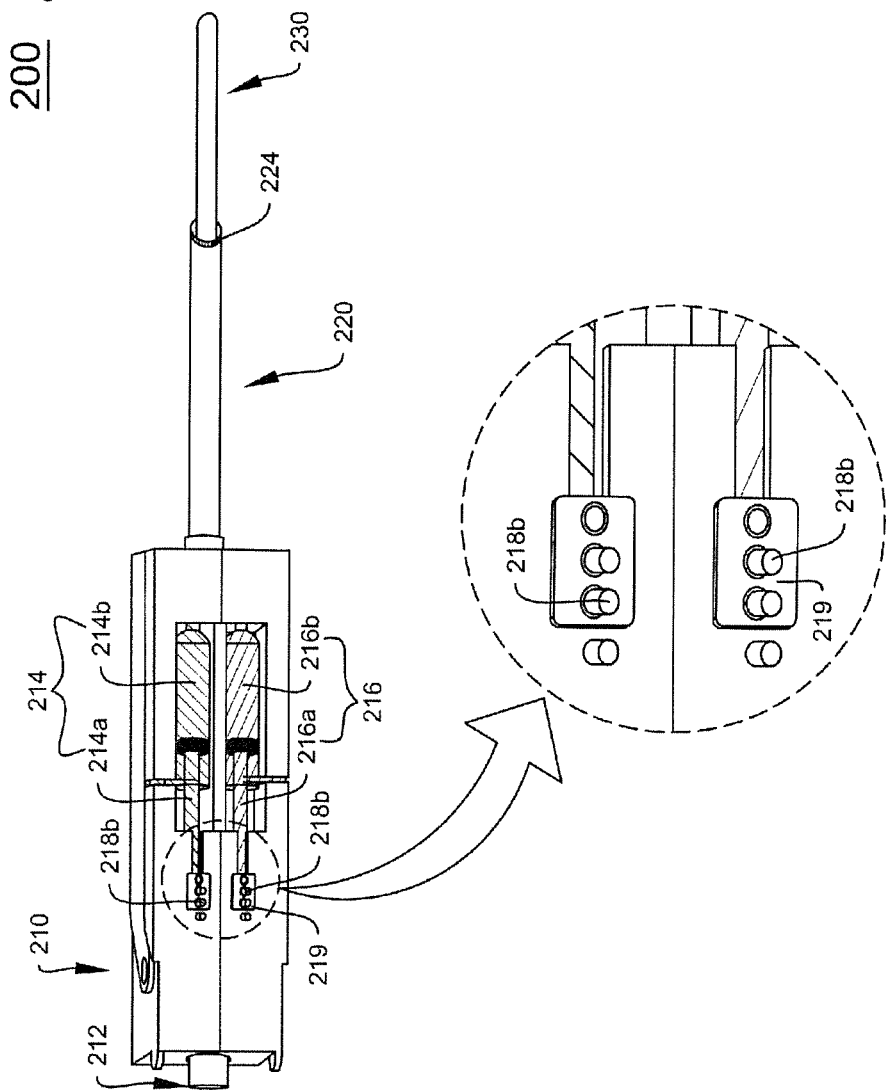
[Fig. 4]

[Fig. 5]
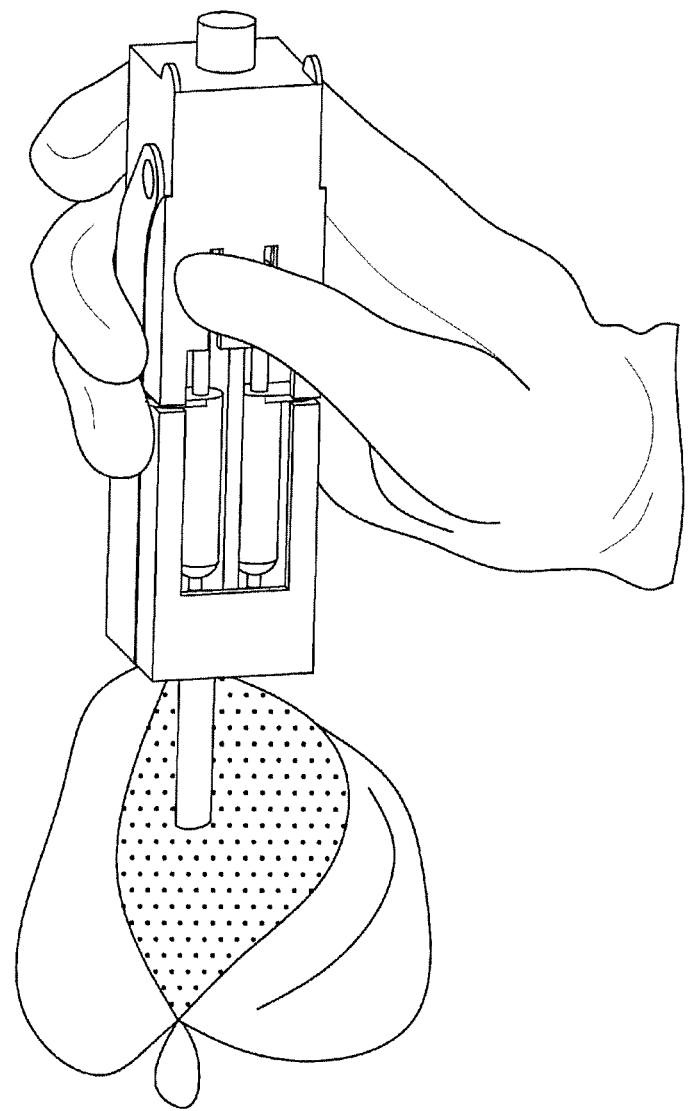

[Fig. 6]
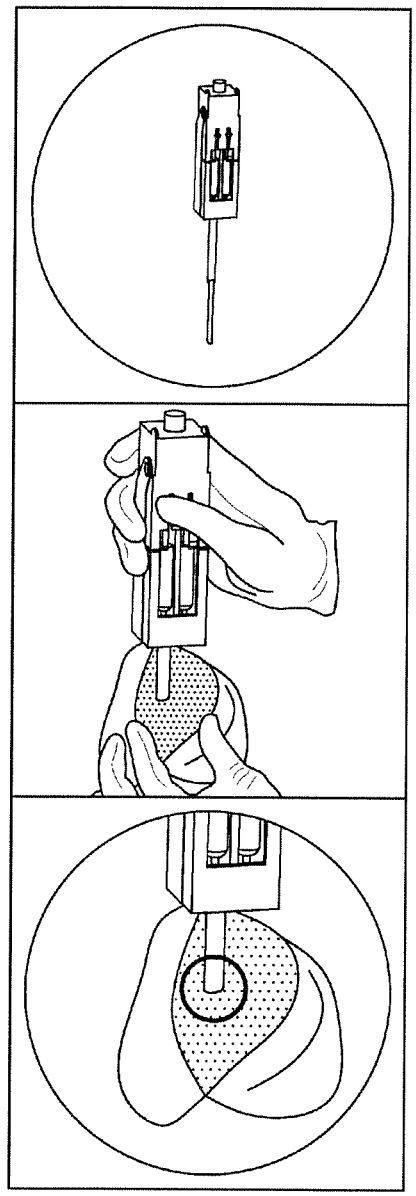

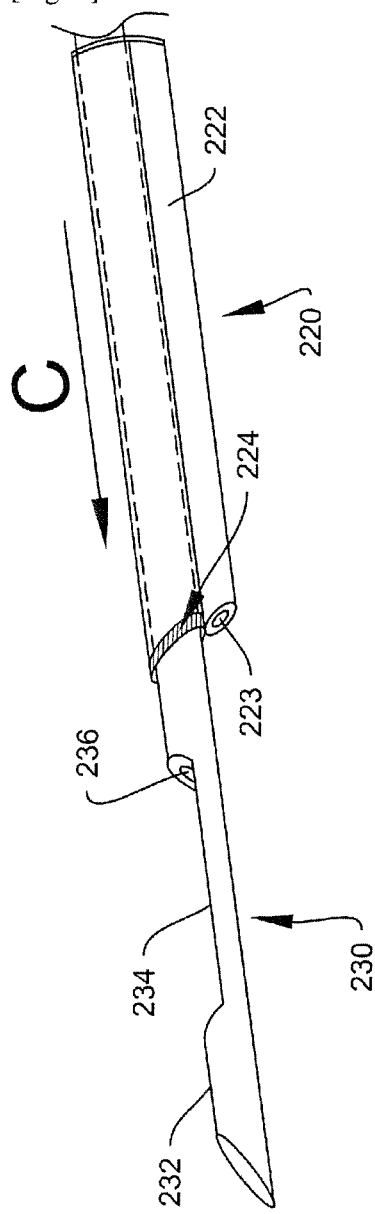

[Fig. 8]
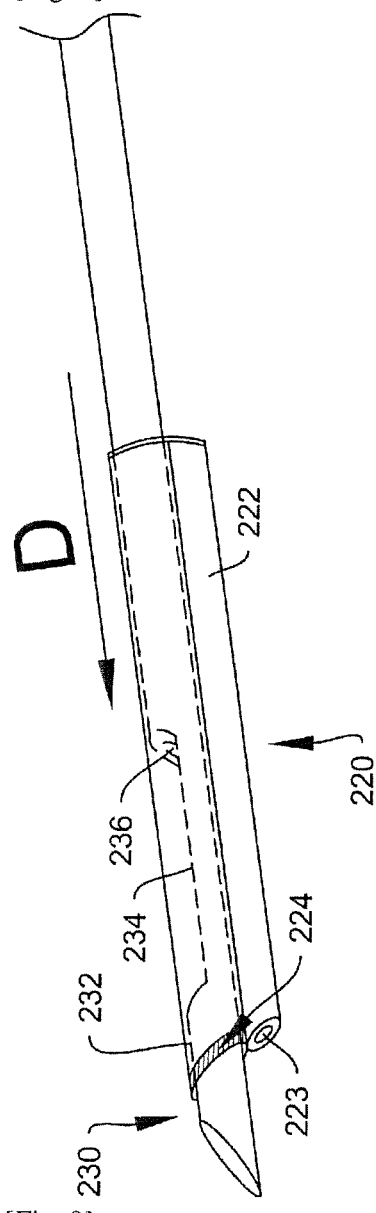
[Fig. 9]
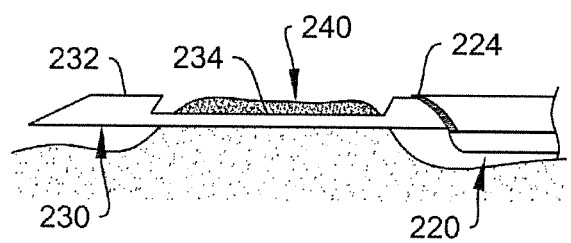

[Fig. 10]
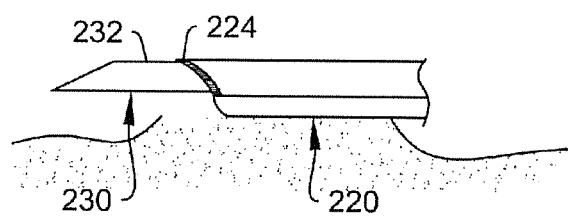
[Fig. 11]
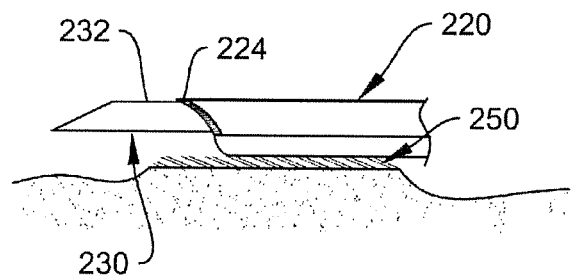
[Fig. 12]
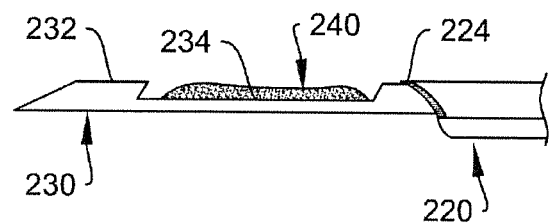

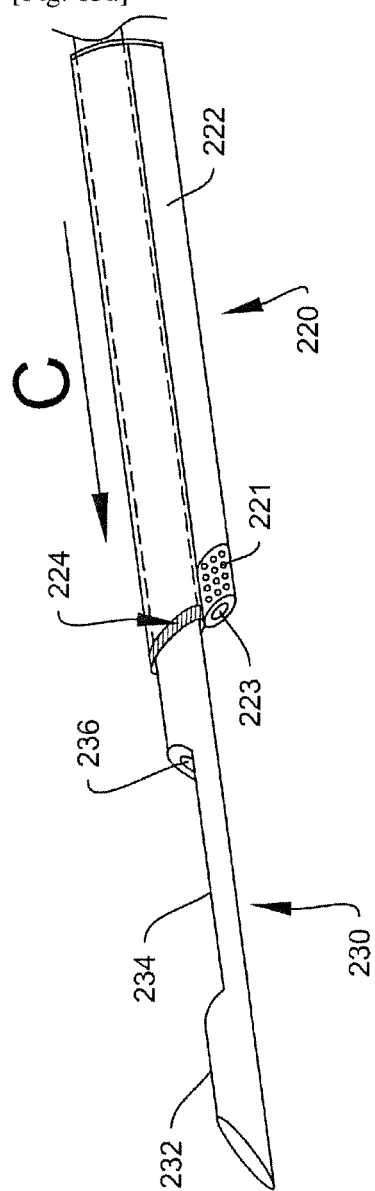
[Fig. 13a]

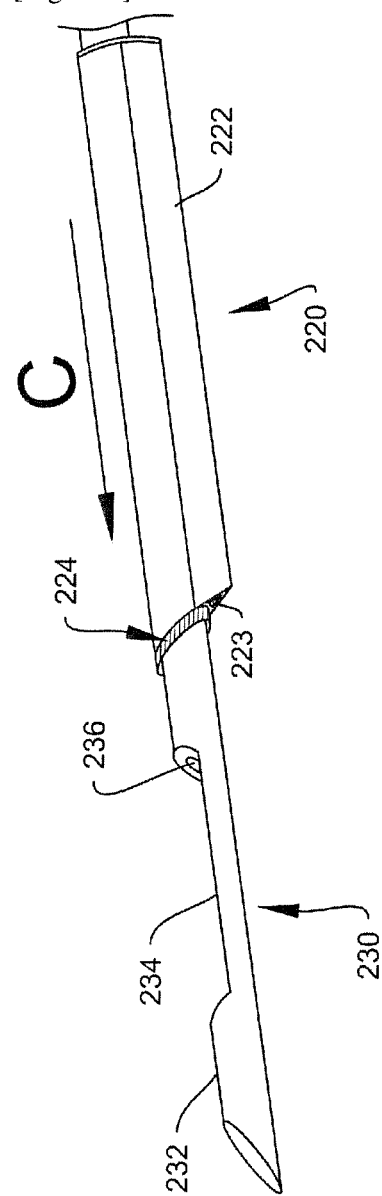

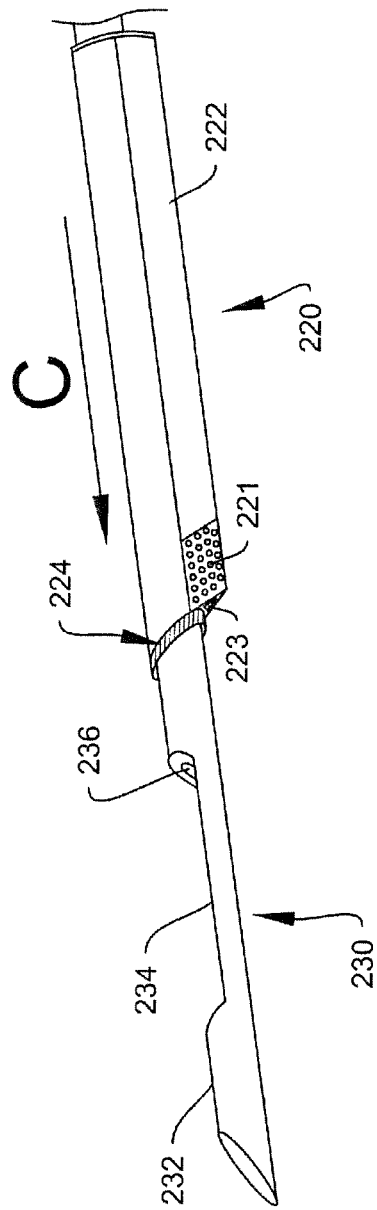
[Fig. 13c]
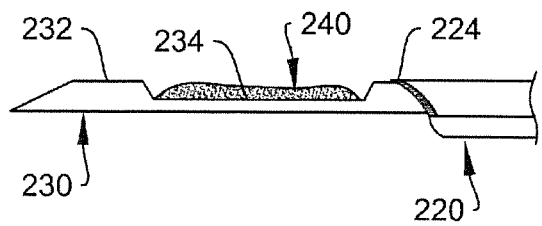
[Fig. 14a]

[Fig. 14b]
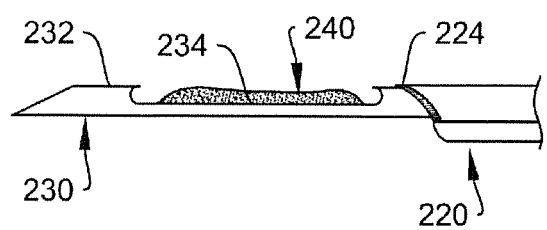
[Fig. 14c]
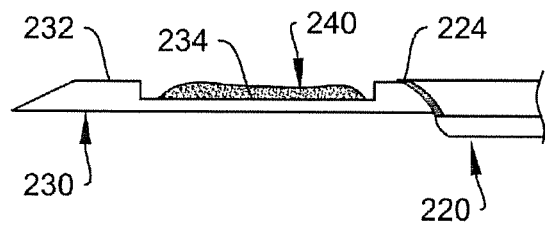
[Fig. 14d]
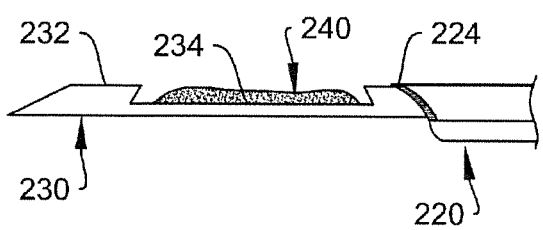

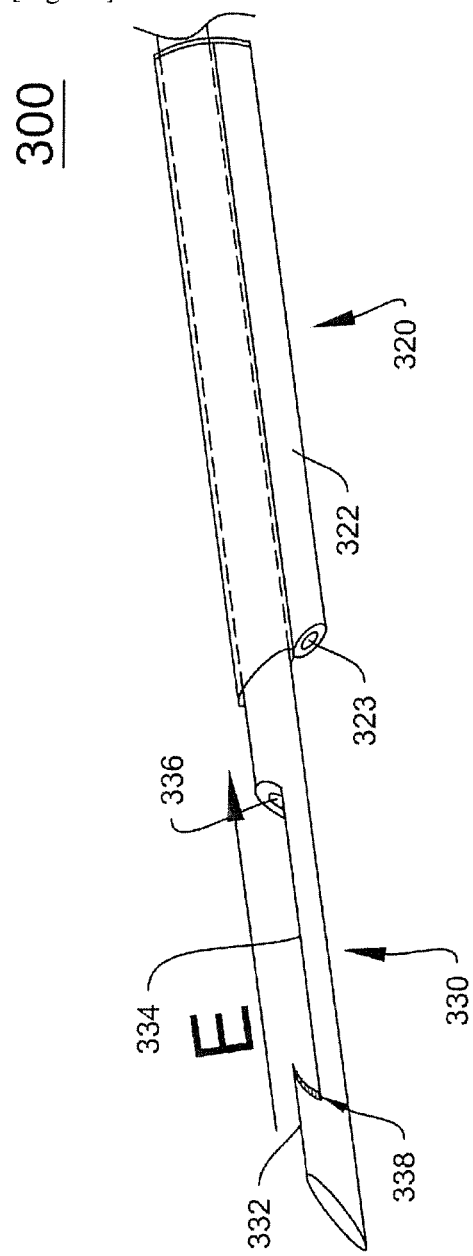
[Fig. 15]

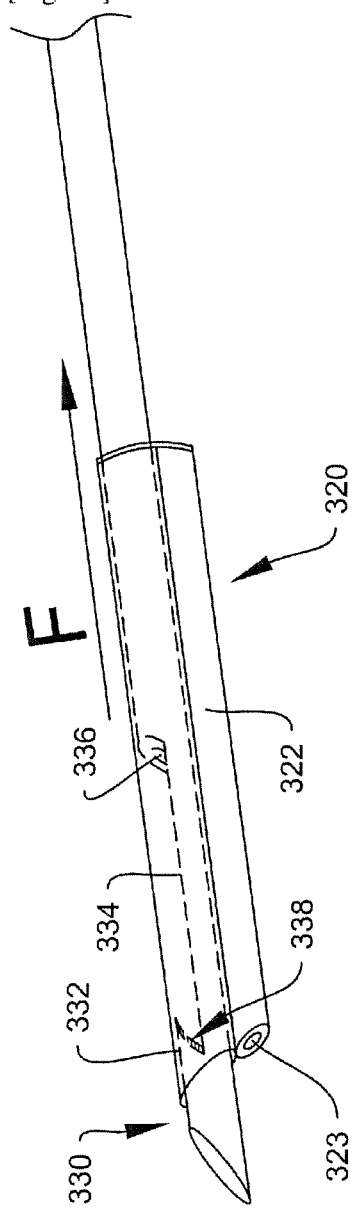

[Fig. 17]
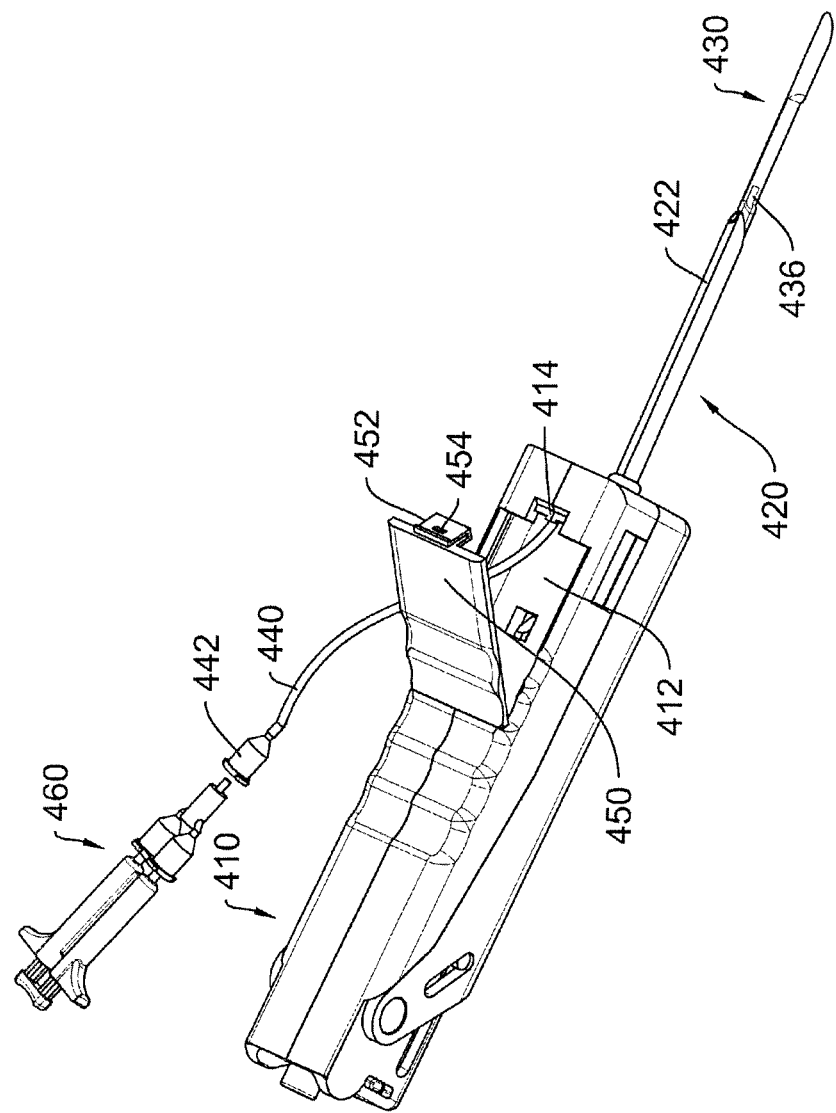

[Fig. 18]
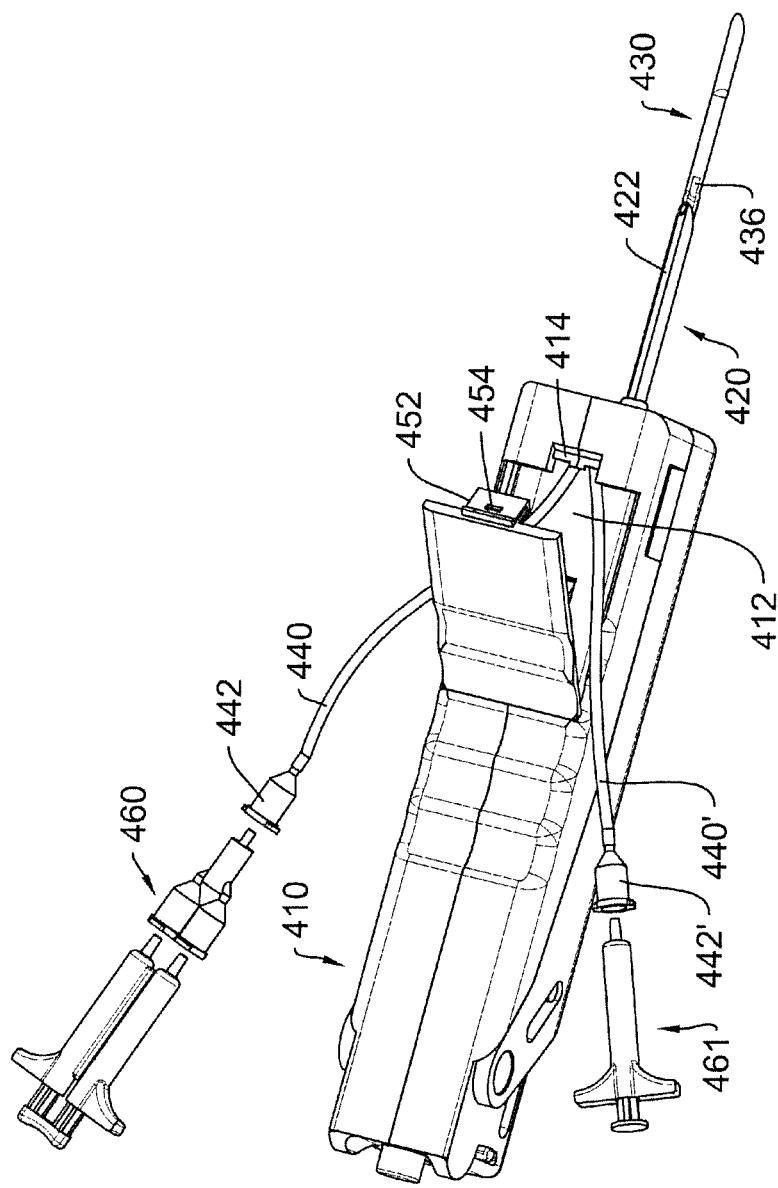

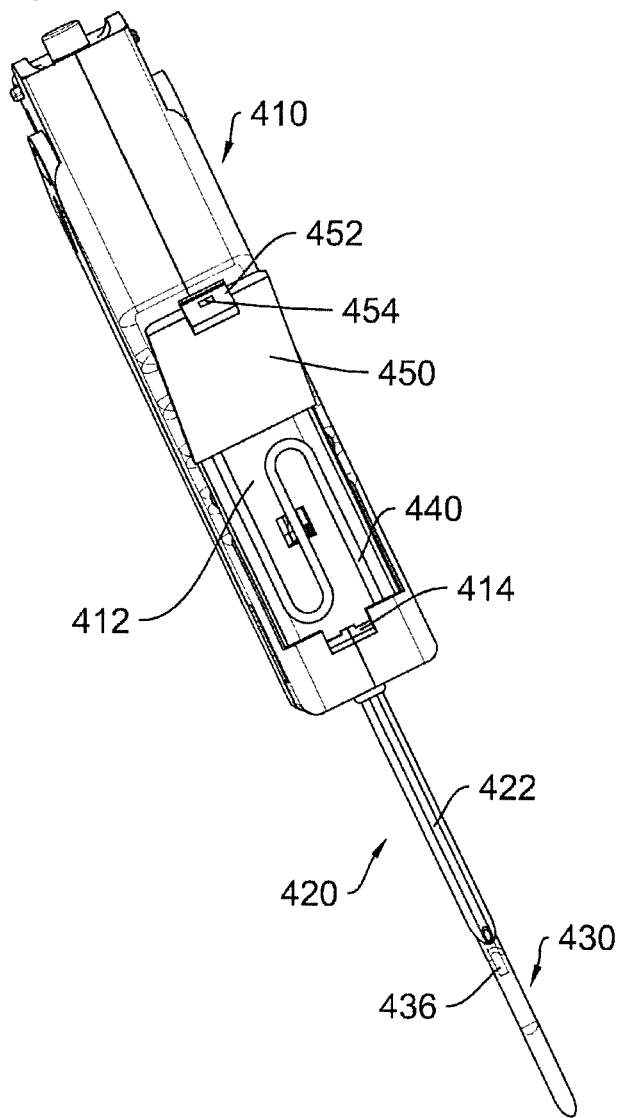
[Fig. 19]

BIOTISSUE SAMPLING APPARATUS

TECHNICAL FIELD

The present disclosure relates to a sampling biopsy device, and a biotissue sampling apparatus and the method thereof for simultaneous tissue sampling and medicine injection.

BACKGROUND

Various types of tumors developing in a body need accurate diagnosis because medicine and method for treatment may be different. Definite diagnosis of a tumor is diagnosed by detecting tumor cell in a tumor tissue. However, various types of tumors may develop in the same area of the body, thus identifying the type of a tumor through cytoscopy before treatment is required.

Methods for tissue biopsy at a tumor lesion are incision biopsy that makes an incision in the skin and sample a tissue, fine needle aspiration biopsy that uses a syringe and, a gun biopsy that use a needle firing device.

An incision biopsy may have high accuracy of diagnosis because enough tissue can be sampled. However, incision biopsy is costly and time-consuming due to anesthesia and skin incision. Further, without accurate and attentive surgery, there is a high possibility of contamination of a tumor tissue around the incision area.

A fine needle aspiration biopsy is less discomforting and painful for the patient. However, accurate diagnosis may be difficult because the amount of sampling is too small.

A gun biopsy is possible of obtaining more tissue sample using a needle with an incisal surface. Thus, accuracy of diagnosis is relatively high among biopsy methods. Therefore, the gun biopsy is widely used in diagnosis of various cancers.

FIG. 1 illustrates a perspective view of a biotissue sampling apparatus 100 according to a gun biopsy technology of a related art.

A biotissue sampling apparatus 100 according to a biopsy technology of a related art includes a housing 110, a tube extending and combining with a front-end of the housing 110 and a needle assembly 130 that sample a body tissue through combining with a front-end of a tube 120.

The needle assembly 130 includes a front-end 132 and a storage unit 134 storing a tissue formed in the back of a front-end 132.

A firing button 112 formed on the rear-end of the housing 110 moving the needle assembly 130 to a biopsy area and advances the tube according to the moved needle.

A cutting unit 122 is formed on the front-end of the tube 120 to cut a tissue.

A method for use of a biotissue sampling apparatus 100 according to a related technology of the afore-mentioned structure is illustrated at the following.

FIG. 2A to FIG. 2C are tissue sampling process of a biotissue sampling apparatus 100 according to a related art.

First, insert a tube 120 in a tumor tissue while looking at an imaging device (not shown) then when pushing a firing button 112 one time that is formed on a rear-end of a housing, a needle assembly 130 penetrates into a tissue area for sampling. Thereby, a tissue for sampling is placed in a storage unit 134 of the needle assembly. (refer to arrow A of FIG. 2A)

When the tissue is placed in the storage unit 134, push the firing button 112 formed in the rear-end of the housing 110 and the tube 120 moves to the front-end of the needle assembly 130 as shown in FIG. 2B. Thereby, the tissue is cut and put it in the storage unit 134. (refer to arrow B of FIG. 2B)

Lastly, after the tube 120 is extracted from the skin while the tube 120 is moved to the front-end 132 of the needle assembly 130 (FIG. 2B), a sampled tissue may be stored in the storage unit 134 of the needle assembly 130 may be obtained. Thus, tissue sampling is completed as illustrated in FIG. 2A.

However, a biotissue sampling apparatus 100 of related art with the above structure may cause hemorrhage in an inserting hole when a needle assembly 130 is inserted and extracted from a body. Thus, if blood pools, bruise or hematoma may be a problem.

Further, when a tissue is a malignant tumor, a hemorrhage area and hematoma may be regarded as a contamination by a malignant tumor cell. Thus, a cutting range may be expanded or may have to carry out dismemberment during surgery.

Additionally, two cases of fluid and solid substance mixed disparately in a body tumor and a cystic tumor that only includes fluid exist. In case of a fluid tumor, sampling with a biotissue sampling apparatus according to a related art may not be easy.

SUMMARY OF INVENTION

Solution to Problem

In an effort to solve the problem of related art, the following description provides a biotissue sampling apparatus including a storage unit configured to store a cut tissue in a needle assembly of a biotissue sampling apparatus, an aspirating hole configured to sample a fluid tissue, and an injecting hole configured in a lower unit of a tube injecting medicine in a tissue with a wound, thereby sampling tissue with one device and medicine administration in a region of possible hemorrhage at the same time are possible.

Further, the following description discloses a biotissue sampling apparatus including an aspirating hole configured to administer medicine in a tissue with a wound in a longitudinal direction of a lower part of a tube, thereby enable tissue sampling and medicine injection simultaneously. Thus, prevent the spread of tumor or tissue cell and indicate a sampling track (i.e. a route of a biotissue sampling apparatus was put in) and a tumor region for convenience in cutting during surgery.

Further, the following description discloses a biotissue sampling apparatus that can sample with a storage unit when the tissue to sample is solid and sample with an aspirating hole when the tissue to sample is fluid.

Technical Solutions

The following description provides a biotissue sampling apparatus comprising a housing, a firing button configured on a rear-end of the housing; a tube with an aspirating hole configured to inject medicine in a tissue according to a longitudinal direction of a lower end and extended from a front-end of a housing; and a needle assembly that may move from the tube to a biopsy region by a button thereby cut a solid tissue and store or aspire a fluid tissue.

Further, the following description provides a biotissue sampling apparatus including a cutting unit configured on a front-end of the needle assembly for tissue cutting.

Further, the following description provides a biotissue sampling apparatus including the needle assembly formed with at least one metal selected from a group comprised of Ti, Ni, Fe, Cr, Ta, stainless steel and a shape-memory alloy.

Further, the following description provides a biotissue sampling apparatus including the front-end of the needle assembly coated with at least one metal selected from a group comprised of Ti, Ni, Fe, Cr, Ta, stainless steel and a shape-memory alloy.

Further, the following description provides a biotissue sampling apparatus including a cutting unit configured on a front-end of the tube for tissue cutting.

Further, the following description provides a biotissue sampling apparatus including a storage unit extending from the front-end of the needle assembly, thereby stores the cut tissue.

Further, the following description provides a biotissue sampling apparatus including an aspirating hole connected to a storage unit to aspire a fluid tissue.

Further, the following description provides a biotissue sampling apparatus including a vertical section of the injecting hole is a circle, an oval or an inverted triangle.

Further, the following description provides a biotissue sampling apparatus including an external section of an injecting hole with a plurality of side holes.

Further, the following description provides a biotissue sampling apparatus including a medicine injection syringe connected to an injecting hole and a tissue aspirating syringe connected to an aspirating hole are formed attachable inside a housing.

Further, the following description provides a biotissue sampling apparatus including a medicine injection syringe and a tissue aspiring syringe comprise a hollow syringe body and a piston moving in a syringe body.

Further, the following description provides a biotissue sampling apparatus combining a slide button and a piston enabling a medicine injection syringe and a tissue aspiring syringe to slide.

Further, the following description provides a biotissue sampling apparatus including a medicine injection syringe and a tissue aspiring syringe with a dose of 1 cc to 3 cc.

Further, the following description provides a biotissue sampling apparatus including at least one fixation groove serially formed on one side of the housing where a slide button moves, thereby a piston slides in a unit length. Then stop the piston to prevent moving to a firing button direction due to pressure.

Further, the following description provides a biotissue sampling apparatus including a space unit formed in the housing, one end connected to an injecting hole and an extending tube stored in the space unit.

Further, the following description provides a biotissue sampling apparatus including the other end of an extending tube exposed to outside of the space unit thereby forming a joint unit.

Further, the following description provides a biotissue sampling apparatus including cover configured to open and close the space unit.

Further, the following description provides a biotissue sampling apparatus including a space unit formed in a housing, and one end connected to an aspirating hole and an extending tube stored in a space unit.

Further, the following description provides a biotissue sampling apparatus including the other end of an extending tube exposed to outside of a space unit forming a joint unit.

Further, the following description provides a biotissue sampling apparatus forming a cover that open and close a space unit.

Effects of Invention

A biotissue sampling apparatus according to the present description comprises a needle assembly including a storage unit storing cut tissue, and an aspirating hole sampling a fluid tissue is formed in a lower unit of a tube, and an injecting hole injecting medicine in a tissue with a wound. Medicine is injected by an injecting hole to a hemorrhage in a tumor and biopsy track due to tissue sampling, thereby tissue sampling and medicine injection can be administered simultaneously. Thus, hemorrhage after tissue sampling and contamination of tumor cell may be prevented.

Further, the following description relates to a biotissue sampling apparatus coating medicine on a biopsy track and a tissue sampling region of a tumor, thereby displays a cutting region. Thus, cutting not only a tumor tissue but also a region with coated medicine during surgery.

Further, a biotissue sampling apparatus that sample at a storage unit when a tissue is solid and a fluid tissue may be easily sampled with an aspirating hole.

BRIEF DESCRIPTION OF THE DRAWINGS

FIG. 1 is a perspective view illustrating a biotissue sampling apparatus according to a related art.

FIG. 2A to FIG. 2C illustrate a method for biotissue sampling apparatus according to a related art.

FIG. 3 is a perspective view illustrating a biotissue sampling apparatus according to an embodiment of the present description.

FIG. 4 is a perspective view illustrating a biotissue sampling apparatus according to another embodiment of the present description.

FIG. 5 is a perspective view illustrating a biotissue sampling apparatus according to an embodiment of the present description.

FIG. 6 is a perspective view illustrating an operation of a needle assembly according to FIG. 5.

FIG. 7 to FIG. 12 are a perspective view illustrating a sampling process of a biotissue sampling apparatus.

FIG. 13A to FIG. 13C are a schematic view illustrating various forms of an injecting hole of a biotissue sampling apparatus of FIG. 7.

FIG. 14A to FIG. 14D are a schematic view illustrating various forms of a storage unit of a biotissue sampling apparatus of FIG. 12.

FIG. 15 is a perspective view of a biotissue sampling apparatus according to another embodiment; and, FIG. 16 is a plane view illustrating an operation of a needle assembly according to FIG. 15.

FIG. 17 is a perspective view illustrating a biotissue sampling apparatus according to another embodiment of the present description;

FIG. 18 is a perspective view illustrating a biotissue sampling apparatus according to another embodiment of the present description.

FIG. 19 is a perspective view illustrating a method for installing an extending tube in a storage unit with a closing and opening device.

METHOD FOR CARRYING OUT THE INVENTION

Certain exemplary embodiments of the present inventive concept will now be described in greater detail with reference to the accompanying drawings. In the following description, same drawing reference numerals are used for the same elements even in different drawings. The matters defined in the description, such as detailed construction and elements, are provided to assist in a comprehensive understanding of the present inventive concept. Accordingly, it is apparent that the exemplary embodiments of the present inventive concept can be carried out without those specifically defined matters. Also, well-known functions or constructions are not described in detail since they would obscure the invention with unnecessary detail.

FIG. 3 illustrates a perspective view illustrating a biotissue sampling apparatus 200 according to an embodiment of the present description.

A biotissue sampling apparatus 200 according to FIG. 3 includes a housing 210, a tube 220 extending and combining with a front-end of the housing 210, and a needle assembly 230 sampling a body tissue combining in the tube 220.

A rear-end of the housing 210 includes a firing button 212 moving the tube 220 and the needle assembly 230 a first syringe 214 configured to put a fluid tissue, a second syringe 216 to put medicine, a first slide 215 combining with the first syringe 214 enabling slide, and a second slide 217 combining with a second syringe 216 enabling slide.

The firing button 212 is formed with two level button and detailed illustration thereof is in the following.

The first syringe 214 and the second syringe 216 comprises syringe bodies 214A, 216A of a hollow hole and pistons 214B, 216B moving in a syringe body 214A, 216A and formed in a housing 210.

Further, a first slide 215 and a second slide 217 are formed parallel and attachable in the housing 210. The first slide 215 and the second slide 217 combine with one end of pistons 214B, 216B of the first syringe 214 and the second syringe 216. Thereby, the first syringe 214 and the second syringe 216 can slide.

Herein, the housing 210 is the region a user grasp with a hand. Dosage of the first syringe 214 and the second syringe may be more than lee.

Hereinafter illustrates the method for operation of the first syringe 214 and the second syringe 216.

First, illustrating operation of the first syringe 214, an initial state of the first syringe 214 shows that a front-end of a piston 214B of the first syringe 214 is in contact with a front-end of a syringe body 214A of the first syringe 214. Then when the first slide 215 moves the piston 214B of the first syringe 214 in a firing button 212 direction, the front-end of the piston 214B of the first syringe 214 and the syringe body 214A of the first syringe 214 are separated. Thereby, a fluid tissue is aspirated in the syringe body 214A of the first syringe 214. (Refer to FIG. 5)

Herein, when the first syringe 214 aspirates a fluid tissue, a piston 214B of the first syringe 214 generates pressure in a firing button 212 direction. The fluid tissue aspirated in a syringe body 214A of the first syringe 214 has viscosity. Thereby, pressure occurs in an opposite direction to the piston 214B of the first syringe 214. Thus, the pistons 214B, 216B of the syringes 214, 216 that was moving in a firing button direction may move to a needle assembly 230 direction.

Therefore, at least one fixed groove 218 is serially formed on one side of the housing 210 in that the first slide 215 and the second slide 217 slide. Thereby, after sliding the piston in front and back direction and, after stopping, the piston may be stopped to prevent moving to a firing button direction by pressure and can operate in a unit length.

If the fixed groove 218 can prevent pistons 214B, 216B from further moving in the needle assembly 230 direction, it is not especially restricted. However, as illustrated in an enlarged view of FIG. 3, the fixed groove 218A may be a lackgear form and this can prevent the pistons 214B, 216B of the syringes 214, 216 to move in the needle assembly 230 direction.

According to a biotissue sampling apparatus of an embodiment of the present description, as illustrated in FIG. 4, a plurality of fixed groove 218B may be formed in a protrusion form in a longitudinal direction on one side of the sliding housing 210. Further, the fixed hole 219 that may be coupled with the fixed groove 218B may be formed in a rear end of the first slide 215 and the second slide 217. Particularly, as illustrated in an enlarged view of FIG. 4, the first slide 215 or the second slide 217 moves in a longitudinal direction and when the fixed groove 218B is caught and fixed by being inserted in the fixed hole 219, the pistons 214B, 216B may be prevented from being move to a needle assembly 230 direction. Depending on cases, the fixed groove 218B of a protrusion form may formed in one line or two lines according to a moving direction of the first syringe 215 and the second syringe 217. Further, the fixed groove 218B may move in a horizontal direction of the pistons 214B, 216B of the syringes 214, 216 by moving upward and downward by external pressure.

Referring to the operation of the second syringe 216, initial state of the second syringe 216, a piston 216B front-end of the second syringe 216 is separated at a maximum with a syringe body 216A front-end of the second syringe 216. Further, when the second slide 217 moves the front-end of the piston 216B of the second syringe 216 to the front-end of the syringe body 216A, the medicine in the syringe body 216A of the second syringe 216 is injected to a tissue sampling region of a tumor and a hemorrhage region of the tissue sampling track through an injecting hole 222 by a pushing force of a piston 216B of the second syringe 216. (Refer to FIG. 6)

FIG. 17 and FIG. 18 is another embodiment of a biotissue sampling apparatus that may be a structure including at least one extending tube instead of the first syringe and the second syringe.

According to an embodiment, the biotissue sampling apparatus may include a space unit 412 formed in a housing 410 and one end connected to the aspirating hole 436 and/or rear-end of the injecting hole 422, and the extending tubes (440, 440') stored in the space unit 412.

Particularly, when using extending tubes 440, 440', one end of the extending tubes 440, 440' are respectively connected to the rear-end of the aspirating hole 436 and/or the injecting hole 422. The other end is exposed to an outside of the space unit 412. Additionally, the other end may include coupling units 442, 442' for coupling of a one-piece syringe 460 or a general syringe 461.

The one-piece syringe 460 is connected to a coupling unit 442 and the general syringe 461 is coupled with another coupling unit 442'. Thereby, aspirating or medicine injection is possible through the extending tubes 440, 440'. Particularly, when only processing biopsy, extending tubes 440, 440' is stored and kept in the space unit 412. Further, aspirating of fluid may be proceed with a general syringe 461 through the coupling unit 442' and medicine injection may be proceeded through coupling the one-piece syringe 460 with medicine coupling with a coupling unit 440.

In other words, the extending tubes 440, 440' may be used connecting to the rear-end of the aspirating hole 436 or the injecting hole 422 according to purpose of use. Further the extending tubes 440, 440' may be used simultaneously connected to the rear-end of the aspirating hole 436 and the injecting hole 422.

The type of medicine injected in the one-piece syringe 460 may vary. For example, the medicine maybe an anti-cancer drug or a hemostatic. The hemostatic is kept in a fluid form respectively separated in a one-piece syringe 460 and when injecting, the hemostatic is combined and coagulated having hemostasis effect.

Further, the coupling units 442, 442' used in the present description is an universal connector that may install all kinds of syringes. Therefore, the coupling units 442, 442' may be simply and easily installed with various syringes.

Meanwhile when not using the extending tube, as illustrated in FIG. 19, a one-piece syringe or a general syringe may be removed to store the extending tube 440 in a space unit 412 and keep in a biotissue sampling apparatus through a cover 450 that is combined with the space unit 412.

Particularly, the cover 450 may not specially be restricted if the space unit 412 may be a form that can open and close. However, the cover 450 may be formed in one-piece with the housing 410 and the locking protrusion 452 with a certain size groove 454 may be formed in the cover 450 front-end. Thereby, the locking protrusion 452 may be inserted in a hook formed on one side of the space unit 412. Further, the space unit 412 may have a certain depth and size for storage of the extending tubes 440, 440' then the space unit 412 is not specially restricted.

FIG. 7 illustrates a perspective view of a biotissue sampling apparatus 200 according to an embodiment of the present description. FIG. 8 illustrates a plane view of an operation of a needle assembly 230 according to the FIG. 7.

FIG. 7 to FIG. 8 illustrate a biotissue sampling apparatus 200 according to an embodiment of the present description including a housing 210, a tube extending and combining to a front-end of the housing 210, and a needle assembly 230 sampling a body tissue through combining in the tube 220.

The feature and form of a housing 210 is identical with the illustration of FIG. 3, hence omitted.

The needle assembly 230 is formed on a front end unit 232, and a rear direction of the front unit 232 then connected to a storage unit 234 storing tissue and a first syringe 214 at a storage unit 234, thereby forming an aspirating hole 236 sampling fluid tissue.

If the front end unit 232 of the needle assembly 230 is a needle form with a cutting side it is not particularly restricted. Additionally, the front-end unit 232 of the needle assembly 230 may have a triangle pyramid form.

Further, the needle assembly 230 may form with at least one metal selected from a group comprised of Ti, Ni, Fe, Cr, Ta, stainless steel and a shape-memory alloy. Additionally, the needle assembly 230 may be coated with at least one metal selected from a group comprised of Ti, Ni, Fe, Cr, Ta, stainless steel and a shape-memory alloy.

The needle assembly 230 may not have an element that may cause infection because harmful to a body and may be a nickel-titanium alloy of good corrosion resistance and mechanical feature. The nickel-titanium alloy has a formation restoring temperature differing according to a weight ratio. For example, when the formation restoring temperature is higher than a room temperature, a shape memory effect is generated and when the formation restoring temperature is lower than the room temperature, super elastic effect is generated.

If a superelastic alloy is a general metal material, the superelastic alloy may be changed by applying a stress component that is big enough for plastic deformation. Further, when stress component is removed, the superelastic alloy restores into the original form like a rubber. Thus, when sampling a tissue, change or fracture due to sampling force does not occur and maintain the original form even after sampling. Therefore, safety may be improved.

In an effort to produce the effect of the present description, nickel-titanium alloy may have weight ratio between nickel and titanium 55:45 to 99:1 and may also be 55:45 to 65:35. The needle assembly 230 of the present description may be formed by melting the composite with a melting water at a vacuum arc melting furnace and coating only on the front-unit 232 of the needle assembly. More particularly, the needle assembly of the present description may be formed by processing the melted nickel-titanium melting water after coagulating in a board plank form.

Meanwhile, the tube 220 comprises an injecting hole 222 configured for medicine flows through and a cutting unit 224 to cut a tissue and the injecting hole 222 is formed in a longitudinal direction in a lower unit of the tube 220.

The vertical section form of the injecting hole 222 may be variously formed according to needs in circle, oval or inverted triangle form, as illustrated in FIGS. 7 and 13A to 13C. The hole size may be determined in a smaller range than the cutting unit 224 according to a device inserted in a body.

Depending on some cases, a plurality of side holes 221 may be formed on an external side of the injecting hole as illustrated in FIG. 13A and FIG. 13C. Particularly, a plurality of side holes 221 are formed in an entire or part of an external side of the injecting hole 222, thereby medicine may be accurately administered in a region with a wound due to tissue sampling through a hole of the injecting hole 223 and a plurality of side holes 221. Further, the side hole 221 may be formed in a front end of the injecting hole 222 with a length of 10 to 20% according to an entire length of longitudinal direction of injecting hole 222.

Further, a cutting unit 224 configured to cut a tissue is sharply formed on a front end unit of a tube 220, i.e. a tube 220 extending from a storage unit 234 of the needle assembly 230.

Referring to FIG. 8, a method for use of a biotissue sampling apparatus 200 according to an embodiment of the present description discloses that a firing button 212 of a housing 210 is installed with a two level button. Thereby, when a user push the firing button 212 one time, a needle assembly 230 is fired to a tissue for sampling (refer to arrow C of FIG. 7). When pushing the firing button again, the tube 220 moves to a front-end unit 232 of a needle assembly 230 to cover the needle assembly 230 (refer to arrow D of FIG. 8).

The tube 220 moves to the front-end unit 232 of the needle assembly 230 and a tissue is cut and sampled in the storage unit 234 by a cutting unit 224 formed in the front-end unit of the tube 220.

Hereinafter illustrates a tissue sampling process of a biotissue sampling apparatus as afore-mentioned referring to the following drawing.

FIG. 9 to FIG. 12 illustrates a drawing showing a sampling process of the biotissue sampling apparatus 200 according to the present description. Further, FIG. 9 to FIG. 12 illustrates a solid tissue as an embodiment of the present description.

First, load a tube 220 and a needle assembly 230 combined in the tube 220 on the housing 210 using a loading device (not shown) combined with a housing 210. Next, insert the tube 220 in a tumor tissue referring to an ultrasonic or a computer tomography (CT) imaging device.

Hereinafter, when pushing a firing button 212 formed on a rear-end unit of the housing 210 one time, the needle assembly 230 is fired and placed on a tissue to be sampled as illustrated in FIG. 10.

Herein, the tissue 240 to be sampled may be solid or fluid. Thus, when the tissue is fluid, the fluid tissue flows into a first syringe 214 through an aspirating hole 236 when sliding a first slide 215 to a firing button 212 direction.

However, when there is no fluid flowing into the first syringe 214, the tissue 240 to be sampled becomes solid.

Hereinafter, when the needle assembly 230 is placed on the tissue 240 to be sampled, a user pushes the firing button 212 again as illustrated in FIG. 10. The tube 220 with a cutting unit 224 formed on the front-end unit moves to a front-end unit 232 of the needle assembly 230 to cover the storage unit 234 of the needle assembly 230.

Herein, the cutting unit 224 is configured to cut the tissue placed in the storage unit 234. The cut tissue 240 is stored in the storage unit 234. As illustrated in FIG. 14A to FIG. 14D, the storage unit 234 of the cutting unit 224 is a form that may be well stored without being exposed outside but not limited thereto.

In a body, the tissue is cut, thus hemorrhage occurs around the tissue. Therefore, when the second slide 217 slides in a tube 220 direction, the medicine 250 in the second syringe 216 that is connected to the second syringe 217 is injected in a hemorrhage region through an injecting hole 222 as illustrated in FIG. 11. Further, the medicine 250 injected through the injecting hole 222 is applied on a tissue sampling region and hemorrhage region.

Herein, a medicine that can be injected through the injecting hole 222 are hemostatic, tissue setting agent, tissue marking fluorescent material and imaging substance, bone cement, tumor treatment medicine and other tissue treatment substances and etc.

Lastly, when taking the tube 220 out of body, a sampled tissue 240 is stored in the storage unit 234 and the stored tissue 240 is sent to a laboratory for testing.

If the tissue to be tested is a fluid tissue, a needle assembly 230 is placed on a tissue to be sampled as illustrated in FIG. 9. Then, when a first slide 215 slides to a firing button 212 direction, the fluid tissue flows into the first syringe 214 through an aspirating hole 236.

Hereinafter, hemorrhage may occur in a body region where the fluid tissue is sampled in the first syringe 214. Therefore, when the second slide 217 slides in a tube 220 direction, the medicine 250 in the second syringe 216 that is connected to the second syringe 217 is injected in a hemorrhage region through an injecting hole 222 and, the medicine 250 that is injected through the injecting hole 222 is applied on a hemorrhage region.

Lastly, the first syringe 214 is attachable, thereby when testing, the first syringe 214 may be attached from the housing 210 and sent to a laboratory for testing.

FIG. 15 is a perspective view of a biotissue sampling apparatus according to an embodiment of the present description. FIG. 16 is a plane view illustrating an operation of a needle assembly according to FIG. 15.

Referring to FIGS. 15 and 16, the biotissue sampling apparatus 300 applied with the needle assembly according to an embodiment of the present description includes a housing 310, a tube 320 extending and combining with a front-end unit of the housing 310, and a needle assembly 330 configured to sample a tissue by combining in the tube 320, and a cutting unit 338 configured to cut a tissue formed on a front-end unit 332 of the needle assembly 330.

The housing 310, the tube 320 and the structure and form of the needle assembly 330 are identically illustrated in the detailed description of FIG. 3 and FIG. 7 hence, omitted of illustration.

The cutting unit 338 configured to cut a tissue is sharply formed on a front-end unit 332 of the needle assembly 330, i.e. a place extending from the storage unit 334 to the front-end unit 332.

Referring to FIG. 16, a method for a use of a biotissue sampling apparatus 300 according to an embodiment of the present description discloses that a firing button of a housing 310 is installed with a two level button. Thereby, when a user pushes the firing button one time, a needle assembly 330 is fired to a tissue for sampling (refer to arrow E of FIG. 15). When pushing the firing button again, the needle assembly 330 moves in the tube 320. (refer to arrow F of FIG. 16).

The needle assembly 330 moves in the tube 320 and a tissue is cut by a cutting unit 338 placed in the front-end unit 332 of the needle assembly 330 and stored in the storage unit 334.

As afore-mentioned, the biotissue sampling apparatus 200 according to the present description comprises the needle assembly 230 including the storage unit 234 storing cut tissue, and in a lower unit of the tube 210 is formed with the aspirating hole 236 sampling a fluid tissue, and the injecting hole 222 injecting medicine in a tissue with a wound. Medicine is injected by the injecting hole 222 to a hemorrhage in a tumor and biopsy track due to tissue sampling, thereby tissue sampling and medicine injection may be administered simultaneously. Thus, hemorrhage after tissue sampling and contamination of tumor cell may be prevented.

Further, the following description relates to a biotissue sampling apparatus coating medicine on a biopsy track and a tissue sampling region of a tumor, thereby displays a cutting region. Thus, cutting not only a tumor tissue but also a region with coated medicine during surgery.

Further, a biotissue sampling apparatus that sample at the storage unit 234 when a tissue is solid and a fluid tissue may be easily sampled with the aspirating hole 236.

The biotissue sampling apparatus of the present description is illustrated according to an embodiment of the present description however, the scope of the disclosure is defined not by the detailed description, but by the claims and their equivalents, and all variations within the scope of the claims and their equivalents are to be construed as being included in the disclosure.

What is claimed is:

1. A biotissue sampling apparatus comprising:
   a housing;
   a firing button disposed at a rear-end of the housing;
   a tube extending from a front-end of the housing, the tube including an injecting hole to inject medicine in a tissue in a longitudinal direction extending away from the front-end of the housing; and
   a needle that is movably coupled within a hollow longitudinal portion of the tube, the needle having a front-end portion to penetrate tissue and a shaft that is at least partially disposed within the hollow longitudinal portion, the shaft including a storage that extends along a longitudinal portion of the shaft to store a portion of the tissue, wherein the storage has 1) a cutting edge that abuts the front-end portion to cut the portion of the tissue as the storage of the needle moves into the tube in the longitudinal direction towards the front-end of the housing and 2) an aspirating hole that opens within the storage extending along the shaft and into the housing, the aspirating hole to aspirate the portion of the tissue that is stored within the storage,
wherein the needle is movable through the tube in the longitudinal direction extending away from the front-end of the housing into the tissue in response to the firing button being user-actuated.

2. The biotissue sampling apparatus of claim 1, wherein the needle is configured to move away from the front-end of the housing in response to the firing button being user-actuated one time, wherein the needle is configured to move into the tube in the longitudinal direction towards the front-end of the housing in response to the firing button being user-actuated a second time.

3. The biotissue sampling apparatus of claim 1, wherein the storage is a first storage, wherein the housing comprises a second storage formed therein, wherein an internal side of the second storage is fluidly coupled to at least one of the injecting hole and the aspirating hole.

4. The biotissue sampling apparatus of claim 3 further comprising an extending tube that is fluidly couple to the injecting hole or the aspirating hole at the internal side of the second storage.

5. The biotissue sampling apparatus of claim 4,
wherein a first end of the extending tube is fluidly coupled to the injecting hole or the aspirating hole at the internal side of the second storage,
wherein the second storage comprises a cover,
wherein the extending tube is configured to be enclosed within the second storage when the cover is closed, and a second end of the extending tube that is opposite of the first end is configured to be removed from the second storage when the cover is open.

6. The biotissue sampling apparatus of claim 5, wherein the second end of the extending tube is configured to removably couple a syringe.

7. The biotissue sampling apparatus of claim 6, wherein the extending tube is a first extending tube that is fluidly coupled to the aspirating hole at the internal side of the second storage, wherein the biotissue sampling apparatus further comprises a second extending tube that is fluidly coupled to the injecting hole at the internal side of the second storage.

8. The biotissue sampling apparatus of claim 7,
wherein a first end of the second extending tube is fluidly coupled to the injecting hole at the internal side of the second storage,
wherein the first and second extending tubes are configured to be enclosed within the second storage when the cover is closed, and the second end of the first extending tube and a second end of the second extending tube that is opposite of the first end of the second extending tube are both configured to be removed from the second storage when the cover is open.

9. The biotissue sampling apparatus of claim 7,
wherein the second end of the first extending tube is configured to couple to a general syringe and the second end of the second extending tube is configured to couple to a one-piece syringe that includes two hollow syringe bodies to hold two fluids separate from one another and a piston for each syringe body,
wherein the one-piece syringe is configured to mix and inject the fluids into the second extending tube when the pistons are moved into their respective hollow syringe bodies.

10. The biotissue sampling apparatus of claim 1, wherein the needle is formed with at least one metal selected from a group comprised of Ti, Ni, Fe, Cr, Ta, stainless steel, and a shape-memory alloy.

11. The biotissue sampling apparatus of claim 1, wherein the front-end portion of the needle is coated with at least one metal selected from a group comprised of Ti, Ni, Fe, Cr, Ta, stainless steel, and a shape-memory alloy.

12. The biotissue sampling apparatus of claim 1, wherein a vertical section of the injecting hole is a circle, an oval, or an inverted triangle.

13. The biotissue sampling apparatus of claim 1, wherein the tube further comprises a plurality of side holes are each configured to inject the medicine into the tissue in a direction that is different than the longitudinal direction.

14. The biotissue sampling apparatus of claim 13, wherein the injecting hole and the plurality of side holes are formed in a front end of the tube.

15. The biotissue sampling apparatus of claim 1 further comprising
a medicine injection syringe to inject the medicine through the injecting hole and into the tissue; and
a tissue aspirating syringe to aspirate the portion of the tissue that is stored within the storage through the aspirating hole.

16. The biotissue sampling apparatus of claim 15, wherein the medicine injection syringe and the tissue aspirating syringe each have a dose of 1 cc to 3 cc.

17. The biotissue sampling apparatus of claim 15, wherein the medicine injection syringe is formed attachably inside a first portion of the housing and the tissue aspirating syringe is formed attachably inside a second portion of the housing, wherein the first and second portions are separate from one another and adjacent to one another.

18. The biotissue sampling apparatus of claim 17, wherein the medicine injection syringe comprises a first hollow syringe body and a first piston that is configured to move inside the first hollow syringe body and the tissue aspiring syringe comprises a second hollow syringe body and a second piston that is configured to move inside the second hollow syringe body.

19. The biotissue sampling apparatus of claim 18 further comprising
a first slide that is configured to move the first piston inside the first hollow syringe body; and
a second slide that is configured to move the second piston inside the second hollow syringe body, wherein the first and second slides are disposed on top of the housing.

20. The biotissue sampling apparatus of claim 19 further comprising
a first plurality of grooves that are serially formed on top of the housing and in which the first slide is disposed, wherein, in response to moving the first slide from a first groove of the first plurality of grooves to a second groove of the first plurality of grooves, the first slide is configured to enable the first piston to move by a unit length and to stop the first piston to prevent it from continuing to move inside the first hollow syringe body; and
a second plurality of grooves that are serially formed on top of the housing and in which the second slide is disposed, wherein, in response to moving the second slide from a first groove of the second plurality of grooves to a second groove of the second plurality of grooves, the second slide is configured to enable the second piston to move by the unit length and to stop the second piston to prevent it from continuing to move inside the second hollow syringe body.

\* \* \* \* \*